(12) United States Patent
Emslie et al.

(10) Patent No.: US 6,458,345 B1
(45) Date of Patent: Oct. 1, 2002

(54) COSMETIC COMPOSITIONS

(75) Inventors: Bruce Steven Emslie; Graham Andrew Turner, both of Wirral (GB)

(73) Assignee: Unilever Home & Personal Care, USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/848,874

(22) Filed: May 4, 2001

(30) Foreign Application Priority Data

May 8, 2000 (GB) .............................. 0011084

(51) Int. Cl.⁷ .............................. A61K 7/32; A61K 7/00
(52) U.S. Cl. .................. 424/65; 424/400; 424/401; 424/DIG. 5
(58) Field of Search .................. 424/65, 400, 401, 424/DIG. 5

(56) References Cited

U.S. PATENT DOCUMENTS

| | | | |
|---|---|---|---|
| 4,265,878 A | 5/1981 | Keil | 424/68 |
| 4,704,271 A | 11/1987 | Hourihan et al. | 424/66 |
| 5,162,378 A | 11/1992 | Guthauser | 514/785 |
| 5,281,413 A | 1/1994 | Abrutyn et al. | 424/68 |
| 5,885,559 A | 3/1999 | Lee et al. | 424/65 |

FOREIGN PATENT DOCUMENTS

| | | |
|---|---|---|
| EP | 0 295 071 | 12/1988 |
| EP | 0 281 288 | 5/1992 |
| EP | 0 291 334 | 9/1993 |
| WO | 98/17238 | 4/1998 |

OTHER PUBLICATIONS

PCT International Search Report in a PCT application PCT/EP 01/04939.
Derwent Abstract of WO98/17238—published Apr. 30, 1998.

*Primary Examiner*—Shelley A. Dodson
(74) *Attorney, Agent, or Firm*—Kevin J. Stein

(57) ABSTRACT

The sensory attributes and/or visibility of deposits of wax-structured antiperspirant or deodorant sticks in the form of emulsions can vary significantly depending on the formulation employed.

A particularly beneficial balance of attributes is obtained in emulsion sticks by employing a composition comprising a continuous phase which comprises from 10 to 35% volatile silicone oil, and from 5 to 15% non-volatile hydrophobic oil, from 40 to 75% of ta disperse aqueous phase which contains from 1 to 35% of an antiperspirant or deodorant active, from 7 to 25% of a wax structurant, from 0.1 to 10% of an emulsifier, and preferably contains up to 5% insoluble particulate materials, %s being by weight based on the composition.

24 Claims, No Drawings

COSMETIC COMPOSITIONS

FIELD OF THE INVENTION

The present invention relates to cosmetic compositions, more particularly to solid cosmetic compositions, and especially to antiperspirant or deodorant compositions in the form of an emulsion.

BACKGROUND OF THE INVENTION

Topically applied antiperspirant compositions are in widespread use throughout much of the world, in order to enable their users to avoid or minimise visible wet patches on their skin, especially in axillary regions. Antiperspirant formulations have been applied using a range of different applicators, including aerosols, roll-ons, pump sprays, sticks and mushroom applicators, in accordance with the individual preferences of consumers. In some parts of the world, sticks are especially popular. The term stick traditionally indicates a bar of solid material which was usually housed within a dispensing container and which retains its integrity whilst being applied, i.e. a firm stick. When a portion of a firm stick is drawn across the skin surface, a film of the stick composition is transferred onto the skin surface. Although the stick has the appearance of a solid article, the material forming the stick usually comprises a structured liquid phase such that a film of the material is readily transferred onto another surface upon contact under pressure. One class of stick which has been contemplated for antiperspirant or deodorant application comprises an emulsion stick. Such sticks comprise a continuous phase in which is dispersed droplets of a second liquid phase, normally referred to as a disperse phase. The continuous phase is one of hydrophobic or aqueous, and the disperse phase constitutes the other. The antiperspirant or deodorant active is conveniently incorporated within the aqueous phase. The hydrophobic phase can be structured by incorporation of wax structurants, these being materials which typically are solid at ambient temperatures, but which melt or dissolve or disperse into the oils constituting the hydrophobic phase at elevated temperatures, for example selected between 60 and 120° C., depending on the choice of oil and wax. When the mixture of wax structurant and oil cools to below its setting temperature, the oil phase solidifies.

When formulating emulsion sticks, there are a number of factors to be taken into account. Some of the factors are antagonistic. One of the first and very important factors relates to the respective proportions of the two phases. The antiperspirant salts have finite solubility in the aqueous phase, so that antiperspirant efficacy potentially increases as the proportion of the aqueous phase increases. However, any increase in the proportion of aqueous phase in the formulation results in a corresponding decrease in the space available to the hydrophobic phase. In conjunction with the choice of its constituent oil or oils, this affects the ability of the hydrophobic phase to provide a strong supporting continuous phase, and hence the strength and integrity of the stick. Moreover, it affects the ability of that phase to contain beneficial hydrophobic constituents.

Waxes have been commonly used or proposed for use in structuring anhydrous formulations, in which a particulate antiperspirant is suspended in an oil phase, but much less attention has been given to their use to structure emulsion sticks.

The market for underarm products is constantly evolving as consumers' tastes and lifestyles change. One attribute of underarm formulations to which consumers have paid considerable attention in recent years is the extent to which the formulation is visible on the skin, either shortly after application or subsequently throughout the following day. This is commonly referred to as visible deposits. Waxes and antiperspirant salts can give rise to visible deposits on human skin, so that in line with current consumer preferences, it would be desirable to be able to reduce or ideally eliminate them. A related attribute relates to the visibility of the formulation on any clothing, either occurring in the course of its application to the skin or by subsequent transfer by contact of the skin with the clothing. Likewise, it would be desirable to reduce or ideally eliminate visible deposits on clothing.

Some oils are effective carriers for distributing antiperspirant or deodorant actives on the skin, but have little effect on visible deposits. Various other oils can ameliorate the appearance of visible deposits, but the space available for such oils in emulsions is constrained by the proportion occupied by the aqueous phase.

The effect of the oils on the ease with which a firm emulsion stick can be formulated has been mentioned herein before. A further factor relates to the variation in sensory attribute of emulsion sticks made using different oils. Thus, for example, such formulations can have a high drag on passage across the skin or they can show a filmy deposit on the skin. They can appear to be sticky when in the dispensing container or on application to the skin, or they feel greasy.

The prior art contains various publications disclosing sticks containing an aqueous component. Thus, for example U.S. Pat. No. 4,265,878 exemplifies a formulation containing substantially no non-volatile oil. The formulation exhibits high visible deposits. U.S. Pat. No. 5,162,378 discloses emulsions containing an aqueous phase, but without a non-volatile oil. Like '878, it provides no teaching on the problems associated with formulations containing non-volatile oils and how to solve them. U.S. Pat. No. 4,704,271 discloses formulations containing a high proportion of disperse aqueous phase, a continuous phase containing a low proportion of non-volatile oil and a high ratio of volatile to non-volatile oils, structured with stearyl alcohol. This formulation has an intrinsically high level of visible deposits from its active and structurant which is reduced to only a limited extent.

WO 98/17238 exemplifies emulsion formulations containing non-volatile oils that are free from volatile silicones. Consequently, it is silent as to the constraints relating to formulations, which desire to contain both such constituents and the benefits from containing both of them in selected proportions.

EP-A-0291334 circumvents the use of waxes by employing a liquid crystal phase to structure the product. Accordingly, it provides no teaching concerning the provision of wax-structured structured emulsions containing both a volatile silicone and a non-volatile oil.

EP-A-0281288 exemplifies an antiperspirant formulation in which an oil phase containing only a small proportion of a non-volatile oil is structured with stearyl alcohol. Such a formulation exhibits a high drag and indeed also has a relatively high visible deposit. Accordingly, it does not provide teaching on how to address such issues. EP-A-0295071 discloses emulsion sticks employing a disperse phase based on a polyhydric alcohol, which can also contain a minor proportion of water. Propylene glycol is exemplified in a 4:1 weight ratio to water in the disperse phase. Sticks which are based on propylene glycol as the principal lipophobic constituent typically exhibit stickiness.

It is an object of the present invention to provide an emulsion stick formulated to exhibit a desirable combination of sensory attributes, stick integrity and reduction of visible deposits.

SUMMARY OF THE INVENTION

According to one aspect of the present invention there is provided a cosmetic composition in the form of a stick containing an antiperspirant or deodorant active and comprising a continuous hydrophobic phase containing a volatile silicone oil, a non-volatile hydrophobic oil and a wax structurant, a disperse aqueous phase and an emulsifier characterised in that the continuous phase comprises from 10 to 35% volatile silicone oil, and from 5 to 15% non-volatile hydrophobic oil, the disperse phase comprises from 40 to 75%, the antiperspirant or deodorant active comprises from 1 to 35%, the wax structurant comprises from 7 to 25%, the emulsifier comprises from 0.1 to 10%, and the composition preferably contains up to 5% insoluble particulate materials, %s being by weight based on the composition.

By the employment of a composition of constituents selected within the ranges specified hereinabove, it is possible to produce an antiperspirant or deodorant emulsion stick exhibiting a combination of two or more beneficial properties, from the list of avoiding or ameliorating visible deposits, avoiding or ameliorating filmy deposits, avoiding or ameliorating drag, avoiding or ameliorating stickiness, and improving or retaining consumer-acceptable glide, whilst continuing to enjoy an acceptable stick hardness. In other words, it is possible to produce a stick from an emulsion, which is structured using a wax, and which exhibits a number of attributes which are well liked by consumers.

In a related aspect of the present invention, there is provided a process for making the compositions of the first aspect, namely, comprising the steps of forming a hydrophobic mixture by mixing a volatile silicone oil, a non-volatile oil and a wax structurant at an elevated temperature or bringing the mixture to the elevated temperature at which the structurant melts or is dissolved or dispersed in the oils, thereby forming a mobile hydrophobic mixture, simultaneously or sequentially forming an aqueous phase containing water soluble or miscible constituents, shear mixing the mobile hydrophobic mixture with the aqueous phase in the presence of an emulsifier, and any insoluble particulate materials thereby forming an emulsion comprising a hydrophobic continuous phase and a disperse aqueous phase, cooling or permitting the emulsion to cool to a temperature at which a solid is formed by the structurant structuring the continuous phase, characterised in that the continuous phase comprises from 10 to 35% volatile silicone oil, and from 5 to 15% non-volatile hydrophobic oil, the disperse phase comprises from 40 to 75%, the antiperspirant or deodorant active comprises from 0.5 to 35%, the wax structurant comprises from 7 to 25%, the emulsifier comprises from 0.1 to 10%, the composition preferably contains up to 5% insoluble particulate materials, %s being by weight based on the composition.

In a further related aspect of the present invention, the compositions according to the first aspect or made according to the second aspect are applied topically to the skin in order to reduce or prevent perspiration or body odor. Specifically there is provided a method for preventing or reducing perspiration or odors on human skin and particularly in armpits comprising applying topically to the skin an emulsion in the form of a stick containing an antiperspirant or deodorant active comprising a continuous hydrophobic phase containing a volatile silicone oil a non-volatile hydrophobic oil and a wax structurant, a disperse aqueous phase and an emulsifier characterised in that the continuous phase comprises from 10 to 35% volatile silicone oil, and from 5 to 15% non-volatile hydrophobic oil, the disperse phase comprises from 40 to 75%, the antiperspirant or deodorant active comprises from 1 to 35%, the wax structurant comprises from 7 to 25%, the emulsifier comprises from 0.1 to 10%, the composition preferably contains up to 5% insoluble particulate materials, %s being by weight based on the composition.

DETAILED DESCRIPTION OF THE INVENTION

The present invention relates to aqueous emulsions in stick form in which an oil phase is structured by a wax.

The relative proportions of the aqueous and oil phases in emulsions according to the present invention are carefully chosen so as to achieve a balance of properties. The proportion of the aqueous phase is normally within the range of from 30 to 70% by weight, taking into account any material present which is dissolved in or forms a single phase with water. Preferably, the aqueous phase constitutes not more than 65 wt. % of the composition and in many desirable embodiments is in the range of from 45 to 60 wt. %. Many favored compositions contain in the region of 50 wt. % aqueous phase.

The content of water in the aqueous phase is often from 40 to 75 wt. % of the phase, and often not more than 65 wt. %. In practice, the proportion of water is often from 20 to 40 wt. % of the composition and in many instances from 24 to 36 wt. %.

The presence of a significant proportion of water in an emulsion is commonly expected to be perceived by the consumer as having wet and cooling attributes. However, and surprisingly, the instant emulsion sticks have been perceived to resemble anhydrous sticks in those attributes.

The aqueous phase commonly contains, in addition to water, the antiperspirant or water-soluble deodorant. The proportion of such materials is usually at least 0.5 wt. %, often at least 2 wt. %, and in many instances at least 5wt. % and in the same or other instances is up to 30 wt. %. The antiperspirant is preferably present in an amount of at least 10 wt. % and in many preferred emulsions between 20 and 25 wt. %.

Antiperspirant actives for use herein are often selected from astringent active salts, including in particular aluminium salts, zirconium salts and mixed aluminium-zirconium salts, including for each both inorganic salts and organic salts and complexes. Preferred astringent salts include aluminium, zirconium and aluminium-zirconium halides and halohydrate salts, such as chlorohydrates.

Preferred aluminium salts include aluminium halohydrates having the general formula $Al_2(OH)_xQ_y \cdot wH_2O$ in which Q represents chlorine, bromine or iodine, x is from 2 to 5 and x+y=6, x and y being either integers or non-integers and w represents a variable amount of hydration, which may be zero. Activated aluminium chlorohydrates such as those described in EP-A-6739 (Unilever NV et al), may be dissolved in the aqueous phase of the instant emulsions.

A range of zirconium salts which can be employed desirably in antiperspirant compositions herein is represented by the following empirical general formula: $ZrO(OH)_{2n-nz}B_z \cdot wH_2O$ in which z is an integer or non-integer in the range of from 0.9 to 2.0, n is the valency of B, 2−nZ is at least 0, B is selected from the group consisting of halides, including chloride, sulphamate, sulphate and mixtures thereof and w represents a variable amount of hydration, which may be zero. In preferred zirconium salts B represents chloride and z lies in the range of from 1.5 to 1.87. In practice, such zirconium salts are usually not employed by themselves, but as a component of a combined aluminium and zirconium-based antiperspirant, the aluminium component normally being selected in accordance with the above-mentioned formula for halohydrates. Especially desirable salts comprise mixed aluminium-zirconium chlorohydrates, optionally activated.

It will be recognised that the above-identified formulae for aluminium, zirconium and aluminium-zirconium salts are empirical and encompass compounds having coordinated and/or bound water in various quantities as well as polymeric species and mixtures and complexes. In particular, zirconium hydroxy salts often represent a range of salts having various amounts of the hydroxy group.

Antiperspirant complexes based on the above-mentioned astringent aluminium, zirconium and aluminium-zirconium salts can desirably be employed in the present invention. Preferably, aluminium halohydrate and/or zirconium chlorohydrate materials are complexed. The complex often employs a carboxylic acid or carboxylate group, and advantageously an aminoacid. Examples of suitable aminoacids include dl-tryptophane, dl-β-phenylaniline, dl-valine, dl-methionine and β-aniline, and preferably glycine which satisfies the formula $CH_3(NH_2)CO_2H$.

It is highly desirable to employ complexes of a combination of aluminium halohydrates and zirconium chlorohydrates together with aminoacids such as glycine, such as those disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in the range of 2 to 10, especially 2 to 6, a ratio of (Al-Zr) / Cl in the range of 2.1 to 0.9 and a variable amount of an amino acid, particularly glycine. Actives of this preferred type are available from Westwood, Summit and Reheis.

Some formulations may contain activated ZAG complexes which are produced by the process disclosed in U.S. Pat. No. 5,486,347 (Callaghan et al) and which are subsequently dissolved in the aqueous phase of the emulsion.

Other actives which can be utilised comprise aluminium lactates, borate cross-linked aluminium salts, and astringent titanium salts, for example those described in GB 2299506A. Yet other actives includes chlorlinergenics, antihistamines and antiandrenerics.

The proportion of antiperspirant salt in the composition normally excludes the weight of any water hydrated.

It will be recognised that the astringent aluminium and/or zirconium salts and especially aluminium and/or zirconium halohydrates described herein can act to reduce odor generation, for example when present in the composition at a concentration at the lower end of the specified range, such as from 0.5 to 6 wt. %.

It can be desirable to incorporate a minor proportion of a C2 to C6 dihydric or polyhydric aliphatic alcohol, for example in a proportion of up to half the weight of water in the aqueous phase. Normally, the proportion of such a di or polyhydric alcohol is from 0 to 15 wt. %, and especially from 3 to 12 wt. % of the emulsion. Examples of preferred dihydric or polyhydric alcohols include propylene glycol, glycerol or sorbitol. By restricting to incorporation of only a minor proportion of such alcohols, it is possible to further constrain the extent of cooling arising from the aqueous phase and the extent of evaporation and concomitant appearance of visible deposits, without the composition suffering from undue stickiness or other negative sensory attributes that can arise from employing such compounds in an emulsion as the major fluid constituent of the lypophobic phase. Some particularly preferred emulsions contain from 3 to 10 wt. % glycerol.

Although one of the benefits of the emulsions of the instant invention is that the emulsions do not exhibit great cooling, the extent of cooling can be controlled by incorporating a chosen proportion of a volatile monohydric aliphatic alcohol such as ethanol or isopropanol, for example selected in the range of up to 5 wt. %, eg at least 0.1 wt. %. Many preferred formulations, however, are free from volatile alcohols.

The wax structurants employed herein may comprise any natural or synthetic wax and as such can be derived from plants or animals or synthesised. Many natural waxes are themselves a mixture of different generic classes of molecule and mixtures of several members of such classes. The waxes can also be selected from components of natural waxes which are themselves waxy or from derivatives of waxes which are themselves waxy. The waxes have a melting point which is usually at least 35° C. and normally not above 95° C. Many waxes melt in the region of 40 to 90° C. It is advantageous to select waxes or blend which melt in the range of from 60 to 85° C. All the waxes may satisfy the melting point conditions, eg in the range 60 to 85° C., or the blend may comprise one or more waxes which melt within the range and one or more which melt above and/or one more which melt below, provided that the average falls within the range. One suitable combination comprises a wax melting in the range of 50 to 65° C. and a second in the range of 65 to 85° C.

One class of wax employable herein comprises fatty alcohols (typically insoluble in water) often containing from 12 to 30 carbons such as stearyl alcohol. Fatty herein indicates a long chain aliphatic group, such as at least 8 or 12 linear carbons, which is frequently not branched (linear) and is typically saturated, but may be unsaturated. It is possible for the fatty acid to contain an hydroxyl group, as in 12-hydroxystearic acid, for example as part of a gellant combination, and to employ amido or ester derivatives thereof. Examples of suitable higher molecular weight alcohols include stearyl or behenyl alcohol and sterols such as lanosterol. However, in many preferred formulations according to the present invention, the wax is substantially free from such fatty alcohols, for example below 2% and especially below 0.5 wt. % fatty alcohols.

Other and preferred classes can comprise hydrocarbon waxes such as paraffin waxes, microcrystalline waxes, ceresin, squalene, and polyethylene waxes (molecular weight typically 200 to 10000). Yet other suitable waxes are waxes derived or obtained from plants or animals such as hydrogenated castor oil (castor wax), carnabau, spermacetti, candelilla, beeswax, modified beeswaxes, and Montan wax and individual waxy components thereof. Such waxes often comprise a mixture of waxy components including one or more of fatty alcohols and esters, fatty acids and esters, and hydrocarbons such as paraffins. The waxes from some plants comprise fatty ester derivatives of polyols, such as glycerol. Mono and especial di and triglycerides are often very desirable. Synthetic glycerides can be obtained as various grades of Synchrowax ™.

Modified waxes employable herein include waxes containing aliphatic alcohols or carboxylic acids which have been esterified by reaction with a fatty carboxylic acid or alcohol, often containing from 12 to 60 carbons, and especially containing 12, 14, 16, 18, 20 or 22 carbons, or mixtures containing such preferred reactants. For example, the product described in J Kokai 58-092605 in which the free acids in beeswax have been so esterified is employable herein. Yet other modified waxes which are employable herein comprise beeswaxes from which free acids have been removed, as by the method described in U.S. Pat. No. 4,948,584. Yet other suitable waxes comprise polysiliconyl beeswaxes, as described in WO 98/09609 or hexanediol-behenyl beeswaxes as described in WO 98/09712.

One particularly desirable class of waxes for use in the present invention is described in WO 00/74640 (Unilever PLC et al). This class comprises organic waxes having a melting point of from 40 to 90° C. containing at least one aliphatic ester satisfying the formula:

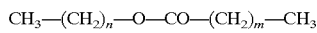

$$CH_3-(CH_2)_n-O-CO-(CH_2)_m-CH_3$$

in which n is from 9 to 39 and m is from 0 to 35.

Such a class of waxes can offer the advantage of comparatively low visible deposits from waxes whilst still enjoying effective structuring capability.

The selected ester, or, more normally, mixtures of esters satisfying the general formula, can comprise, if desired, up to 100% of the wax, with the remainder of the waxes being satisfied by beeswax or one or more of the other waxes indicated hereinabove. In many embodiments, the proportion of the selected ester is at least 70% by weight, preferably at least 80% by weight and most desirably at least 90% by weight of the wax blend.

In some embodiments using this preferred class of wax, it is desirable that it comprises at most no more than a small proportion of free carboxylic acid and hydrocarbons. Preferably, such a wax blend contains no more than about 4% and particularly no more than about 2% by weight non-esterified carboxylic acid. It is highly desirable that the content of hydrocarbons in the wax blend is less, and indeed much less than in a conventional beeswax, particularly is less than 5% by weight and especially from 0 to 2% by weight of the blend.

Within the general formula for the ester, a range of preferred esters comprises those in which n is selected within the range of 14 to 24 and especially 16–20 together with m being selected in the range of 14 to 24 and especially 16 to 20. In second range of preferred esters within the general formula, n is selected in the range of 18 to 38 and m is either 0 or 1. It will be understood that mixtures of esters within each preferred range or mixtures of one preferred range of esters with the other can be employed. Convenient mixtures include a mixture of a wax comprising esters of n=14 to 20 and m=14 to 20 with a wax comprising esters of n=16 to 20 and m=14 to 20 or preferably 16 to 20.

Esters in accordance with the formula given herein can be obtained by a conventional esterification reaction carried under conventional reaction conditions described in the literature for reaction between an alcohol having the chain length appropriate to provide "n" in the ranges specified above and a carboxylic acid having a chain length appropriate to yield "m" in the ranges specified above.

The waxes described herein can be employed by themselves or mixtures of any two or more thereof can be employed, at the discretion of the emulsion producer. One suitable combination comprises castor wax and a paraffin wax, for example in a weight ratio range of from 3:2 to 3:1.

The proportion of wax structurant in the formulation is in some embodiments selected in the range of at least 8%, in some or other embodiments up to 20%, and in certain preferred embodiments from 10 to 15%, %s being by weight based on the formulation.

The hydrophobic carrier liquids employed in the invention emulsions comprise a mixture of a volatile silicone oil and a non-volatile oil, the proportions of the two constituents being selected within prescribed ranges.

The proportion of volatile silicone oil is preferably not higher than 25 wt. % and often within the range of from 10 to 20 wt. %. The proportion of non-volatile oil is preferably at least 8 wt. % and in many instances is not more than 12 wt. %. It is desirable to consider not only the absolute proportion of the oils in the emulsion, but also their relative proportions. Preferably, the volatile silicone oil is present in a weight ratio to the non-volatile oil of at least 1:1 and especially at least 5:4. The ratio is preferably not higher than 3:1 and more preferably not higher than 2:1. By carefully considering the ratio as well as the absolute proportions of the volatile silicone and non-volatile oils, it is possible to combine the benefits of reducing visible deposits, and simultaneously avoiding excess drag and greasiness for the emulsion.

It is further desirable to consider their ratio to the materials which contribute to visible deposits, such as any astringent salt (eg the antiperspirant salt) and/or the wax structurant. It is preferable for the weight ratio of antiperspirant salt to non-volatile oil be selected within the range of from 1:1 to 4:1 and especially from 2:1 to 10:3, whilst retaining the absolute proportion of the non-volatile oil within the proportions described hereinabove.

The volatile silicone oil is often described as a volatile polyorganosiloxane, and is a liquid material having a measurable vapor pressure at ambient conditions (about 20 to 25° C.). Typically the vapor pressure of volatile silicones lies in the range of from 1 or 10 Pa to 2 kPa at 25° C. Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $1 \times 10^{-5}$ m$^2$/sec (10 centistokes), and particularly above $1 \times 10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345 244, 245 and 246, (from Dow Corning Corporation) Silicone 7207 and Silicone 7158 (from Union Carbide Corporation) and SF1202 (from General Electric [US]).

The non-volatile oil can comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series having a viscosity of at least 50 centistokes.

The non-volatile oils can additionally or alternatively be silicon-free. One class of such oils comprises liquid aliphatic hydrocarbons such as mineral oils or hydrogenated polyisobutene, often selected to exhibit a low viscosity. Further examples of liquid hydrocarbons comprise polydecene, hydrogenated polydecene, and isoparaffins containing at least 10 carbon atoms and often in the region of up to 30 carbons.

Other suitable non-volatile oils comprise liquid aromatic esters. Suitable liquid aromatic esters, desirably have a melting point of below 20° C., and include fatty alkyl benzoates. Examples of such esters include suitable C8 to C18 alkyl benzoates or mixtures thereof.

Other non-volatile oils which can be considered to provide a fraction of the non-volatile constituent for example up to 30 % wt. of that constituent for lower melting point waxes, such as those at up to 65° C., but possibly at least a major fraction for higher melting point waxes such as those at 70° C. or higher, may comprise aliphatic ester oils containing at least one long chain alkyl group, such as esters derivable from $C_{1-C20}$ alkanols esterified with a $C_8$ to $C_{22}$ alkanoic acid or $C_6$ to $C_{10}$ alkanedioic acid. The alkanol and acid moieties or mixtures thereof are preferably selected such that they have a melting point of below 20° C. Suitable esters include isopropyl myristate, lauryl myristate, isopropyl palmitate, diisopropyl sebacate and diisopropyl adipate. Other classes of such non-volatile oils like the aliphatic esters include aliphatic branched fatty alcohol oils containing at least 12 and preferably up to 30 carbons, such as isostearyl alcohol or octyldodecanol and liquid aliphatic ethers derivable from at least one fatty alcohol, such as myristyl ether derivatives e.g. PPG-3 myristyl ether or lower alkyl ethers of polyglycols such as PPG-14 butyl ether.

Herein, the emulsion is normally a water-in-oil emulsion. The presence of an emulsifier enables the aqueous phase to form a dispersion. The emulsifier is usually considered to form the interface between the oil and water phases and accordingly its weight is not calculated within either phase.

The proportion of emulsifier or emulsifier system, i.e. combination of emulsifiers, in the emulsion is often selected in the range of from 0.1 to 10% w/w, and in many instances from 0.25 to 5% w/w. More preferred is an amount of from 0.1 or 0.25% up to 3% w/w and especially from 0.5 to 2 wt. %. It is desirable to employ an emulsifier or emulsifier system providing an overall HLB value in a range of from 2 to 10 and preferably from 3 to 8.

It may be convenient to employ either a single emulsifier of suitable HLB, or an emulsifier system employing in combination an emulsifier having an HLB value above a desired overall value and one having an HLB value below the desired value. By employing the two emulsifiers together in appropriate ratios, it is readily feasible to attain a weighted average HLB value that promotes the formation of an emulsion.

Many suitable emulsifiers are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of emulsifiers include ceteareth-10 to -25, ceteth-10–25, steareth-10–25, and PEG-15–25 stearate or distearate. Other suitable examples include C10–C20 fatty acid mono, di or tri-glycerides. Further examples include C18–C22 fatty alcohol ethers of polyethylene oxides (8 to 12 EO). The co-emulsifiers, which typically have a low HLB value, and often of from 2 to often comprise mono or possibly fatty acid diesters of polyhydric alcohols such as glycerol, sorbitol, erythritol or trimethylolpropane. The fatty moiety is often from C14 to C22 and is saturated in many instances, including cetyl, stearyl arachidyl and behenyl. Examples include monoglycerides of palmitic or stearic acid, sorbitol mono or diesters of myristic palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in C1 to C12 alkyl groups.

Suitable emulsifiers are widely available under many tradenames including Abil ™, Arlacel ™, Brij ™, Cremophor ™, Dehydrol ™, Emerest ™, Lameform ™, Quest PGPR ™, Pluronic ™, Prosorine ™, Span ™, Tween ™, SF 1228, DC3225C and Q2-5200.

It is desirable to include at least one particulate insoluble material of small particle size, preferably in a proportion of up to 5 wt. %, and particularly from 1 to 5 wt. %. Such insoluble materials can be inorganic, such as talc, finely divided silica or clay. Alternatively, the material can be small particulate solid hydrocarbons such as finely divided polyethylene. The presence of such a constituent can improve the glide of the stick.

The invention emulsions can additionally contain, if desired, one or more cosmetic adjuncts, for example those in one or more of the classes that have been employed or described for employment in antiperspirant or deodorant formulations. These can include skin benefit agents, such as allantoin or lipids, such as in an amount of up to 3%, colors or skin cooling agents, eg menthol, often in an amount of up to 1%, and preservatives or stabilisers such as alkyl parabens, eg in an amount of up to 1%. One especially preferred constituent of many cosmetic formulations herein comprises a perfume oil, which may itself have deodorant properties, often in an amount of from 0.1 to 4 wt. %, and particularly from 0.5 to 2 wt. %.

The emulsion formulations described herein can be made by any of the processes hitherto described or used for making antiperspirant emulsions containing a high internal phase volume, such as at least 40 wt. % internal phase.

One suitable process comprises

1. Incorporating into the wax into a mixture of the volatile silicone and non-volatile oil in an amount sufficient to thicken or structure the oil phase,
2. Rendering the structurant-containing mixture mobile at an elevated temperature, steps 1 and 2 being conducted in sequence or simultaneously.
3. Obtaining an aqueous solution of the antiperspirant or deodorant, optionally containing an emulsifier.
4. Mixing the mobile material produced in step 2 with the aqueous solution of step 3 in the presence of an emulsifier and with shear to form an emulsion at an elevated temperature.
5. Introducing the emulsion whilst still mobile mixture into a dispensing container and
6. Cooling or permitting the emulsion to cool to a temperature at which it solidifies.

In step 2, it is highly desirable to maintain the mixture at the chosen elevated temperature until the wax has been completely dispersed throughout the oil phase and at a temperature which is often 5 to 10° C. above the melting point of the highest melting wax.

In step 3, it is often convenient to introduce an emulsifier into a pre-formed solution containing the antiperspirant salt, but in other instances, a solid antiperspirant can be dissolved in the aqueous phase. The step is often carried out at elevated temperature or the solution is heated to elevated temperature before being mixed in step 4 with the mobile oil phase. The aqueous phase is often heated to within 20° C. of the oil phase.

In step 4, the two liquid phases are mixed together under shear conditions and in the presence of an emulsifier. By so doing, droplets of the dispersed phase are obtained. This step is carried out at a temperature maintained above the solidification temperature of the formulation, and is often selected in the range of from about 50 to 70° C., depending on its constituents.

In step 5, the mobile emulsion in step 4 is introduced into stick dispensers, often called barrels. This can be carried out using conventional cast methods, or alternatively an injection moulding technique may be employed as described in PCT application no PCT/EP 99/07249.

In step 6, the dispensers containing the mobile emulsion are either subjected to forced cooling, for example by being passed though a cooling tunnel or may be simply allowed to cool in ambient air, for example if they have been filled in step 5 by an injection moulding technique that is operated within 3° C. of the normal setting temperature of the formulation.

The invention formulations described hereinbefore, or produced by the above-described process may be applied to the skin using conventional dispensers and in a conventional manner by exposing a length of stick above the rim of the dispensing container and wiping the stick gently across the skin.

Having described the invention in a general manner, specific embodiments thereof will be described more fully by way of example only.

The ingredients employed in the Examples and Comparisons are as follows:

| Abbreviation | Chemical Name | Trade Mark |
|---|---|---|
| vol sil 1 | Volatile Silicone Oil | DC245 |
| oil 2 | PPG-14-butyl ether | Fluid AP |
| oil 3 | C14–16 alkyl benzoate | Finsolv TN |
| oil 4 | Decyl oleate | Cetiol V |
| oil 5 | hydrogenated polyisobutene | Panalene L14E |
| Emulsifier 6 | Cetyl dimethicone copolyol | Abil EM90 |
| Water 7 | demineralised water | |
| Glycerol 8 | Glycerol | |
| Talc 9 | Talc | Suprafino Talc |
| AZCH 10 | Aluminium zirconium pentachlorohydrate (aq 67% actives) | Rezal 67 |
| AZCH 11 | Aluminium zirconium tetrachlohydrex GLY (aq 50% actives) | Zirconal 50 |
| wax 12 | C16–18 alkyl stearate behenate wax, MP 62oC | Koster Keunen K62 |
| PE 13 | finely divided particulate polyethylene | Acumist B18 |
| oil 14 | fragrance | |
| emulsifier 15 | polyglycerol diisostearate | Lameform TGI |
| emulsifier 16 | Polyglycerol polyricinoleate | Quest PGPR |

-continued

| Abbreviation | Chemical Name | Trade Mark |
|---|---|---|
| oil 17 | hydrogenated polyisobutene | Fancol 800 |
| oil 18 | hydrogenated polyisobutene | Fancol 250 |
| oil 19 | 32 carbon di-guerbet ester | Lambent DG 3200 |
| oil 20 | Hydrogenated polydecene | Silkflo 364 NF |
| oil 21 | Isohexadecane | Permethyl 101A |
| wax 22 | Paraffin wax | SP173 |
| wax 23 | Castor Wax | MP80 |

EXAMPLE 1 AND COMPARISONS C1 AND C2

In this Example formulations 1.1 to 1.6 and Comparison C1 were made by the following general method:

A continuous oil phase was prepared by introducing the wax into a mixture of the oils and the emulsifier. The mixture was heated to the range of 80° C. to 100° C. and then maintained in the range of up to approximately 10° C. above the melting point of the wax, with gentle mixing (low shear) in a Silverson mixer until the wax had dissolved. The mixture was allowed to cool to about 80° C. A disperse phase (also referred to as the internal phase) was prepared by heating a solution of aluminium zirconium active antiperspirant in water or a mixture of water and polyol to a similar temperature as the continuous oil phase.

The hot disperse phase was introduced slowly into the oil phase whilst progressively increasing the mixing speed of the Silverson mixer. When the disperse phase had been completely introduced, the formulation was mixed at higher speed for a further 5 minutes, then mixed at a slower speed until it had reached about 10–15° C. above the formulation set temperature, at which point it was poured in the stick barrels and allowed to cool naturally to ambient laboratory temperature.

The formulations and their attributes are summarised in the following Table 1, except for comparison C2 which is conventional wax structured suspension antiperspirant stick. The term u/a indicates underarm.

TABLE 1

| Ingredient | C1 | 1.1 | 1.2 | 1.3 | 1.4 | 1.5 | 1.6 | C2 |
|---|---|---|---|---|---|---|---|---|
| vol sil 1 | 30.65 | 12.6 | 12.6 | 12.6 | 18.5 | 12.6 | 12.6 | |
| oil 2 | 3.35 | — | — | — | — | — | — | |
| oil 3 | — | 8.4 | 8.4 | 8.4 | 12.5 | — | — | |
| oil 4 | — | — | — | — | — | 8.4 | — | |
| oil 5 | — | — | — | — | — | — | 8.4 | |
| emulsifier 6 | 1.0 | 1.0 | 1.0 | 1.0 | 1.0 | 1.0 | 1.0 | |
| Water 7 | — | — | 4.5 | 4.5 | 4.5 | 4.5 | 4.5 | |
| Glycerol 8 | — | 4.5 | — | — | — | — | — | |
| Talc 9 | — | — | — | 2.0 | 2.0 | 2.0 | 2.0 | |
| AZCH 10 | — | 58.0 | 58.0 | 58.0 | — | 58.0 | 58.0 | |
| AZCH 11 | 50.0 | — | — | — | 48.0 | — | — | |
| wax 12 | 15.0 | 12.5 | 12.5 | 12.5 | 12.5 | 12.5 | 12.5 | |
| PE 13 | — | 2.0 | 2.0 | — | — | — | — | |
| oil 14 | — | 1.0 | 1.0 | 1.0 | 1.0 | 1.0 | 1.0 | |
| Characterisation | | | | | | | | |
| Hardness (mm) | 8.4 | 5.9 | 5.7 | 5.7 | 7.4 | 4.1 | 6.1 | 7.3 |
| Whiteness Wool (0 h) | 13 | 18 | 18 | 20 | | | | 36 |
| Wool (24 h) | 72 | 27 | 32 | 23 | | | | 87 |
| Key Sensory data | | | | | | | | |
| Cool | 10 | 30 | 32 | 41 | | | | 14 |
| Flakes | 17 | 1 | 9 | 10 | | | | 14 |
| Drag | 41 | 16 | 14 | 6 | | | | 11 |

TABLE 1-continued

| Ingredient | C1 | 1.1 | 1.2 | 1.3 | 1.4 | 1.5 | 1.6 | C2 |
|---|---|---|---|---|---|---|---|---|
| Cool (2 min) | 15 | 25 | 23 | 33 | | | | 12 |
| Glide (2 min) | 37 | 57 | 42 | 45 | | | | 49 |
| White visible deposits u/a | 25 | 7 | 12 | 11 | | 8 | | 51 |
| Filmy visible deposits u/a | 33 | 6 | 9 | 7 | | | | 38 |
| White deposits (30 min) u/a | 25 | 8 | 6 | 6 | | 5 | | 40 |
| Filmy deposits (30 min) u/a | 23 | 4 | 3 | 3 | | | | 18 |
| Glide (30 min) | 33 | 57 | 43 | 43 | | | | 43 |

EXAMPLE 2

In Example 2, 3 further formulations were made using the method used for Example 1. The formulations are summarised in Table 2 below.

TABLE 2

| Ingredient | 2.1 | 2.2 | 2.3 |
|---|---|---|---|
| wax 12 | 15.0 | 15.0 | 15.0 |
| vol sil 1 | 16.8 | 14.7 | 12.6 |
| oil 3 | 4.2 | 6.3 | 8.4 |
| Glycerol 8 | 10.0 | 10.0 | 10.0 |
| Emulsifier 6 | 1.0 | 1.0 | 1.0 |
| PE 13 | 2.0 | 2.0 | 2.0 |
| AZCH 11 | 50.0 | 50.0 | 50.0 |
| oil 14 | 1.0 | 1.0 | 1.0 |
| Characterisation | | | |
| Hardness (mm) | 5.4 | 8.7 | 6.5 |
| Whiteness | | | |
| Wool (0 h) | 18 | 19 | 17 |
| Wool (24 h) | 16 | 17 | 17 |

EXAMPLE 3

In Example 3, 5 further formulations were made using the method used for Example 1. The formulations are summarised in Table 3 below.

TABLE 3

| Ingredient | 3.1 | 3.2 | 3.3 | 3.4 | 3.5 |
|---|---|---|---|---|---|
| vol sil 1 | 13.05 | 12.9 | 13.35 | 13.2 | 12.9 |
| oil 3 | 8.7 | 8.6 | 8.9 | 8.8 | 8.6 |
| wax 12 | 12.5 | 12.5 | 12.5 | 12.5 | 12.5 |
| PE 13 | 2.0 | 2.0 | 2.0 | 2.0 | 2.0 |
| Glycerol 8 | 4.5 | 4.5 | 4.5 | 4.5 | 4.5 |
| Lameform TGI | 1.25 | 1.5 | — | — | — |
| Quest PGPR | — | — | 0.75 | 1.0 | 1.5 |
| AZCH 10 | 58.0 | 58.0 | 58.0 | 58.0 | 58.0 |
| Hardness | | | | | |
| Penetration (mm) | 9.9 | 10.0 | 6.7 | 6.6 | 7.5 |

EXAMPLE 4

In Example 4, 5 further formulations were made using the method used for Example 1. The formulations are summarised in Table 3 below.

TABLE 4

| Ingredient | 4.1 | 4.2 | 4.3 | 4.4 | 4.5 |
|---|---|---|---|---|---|
| vol sil 1 | 12.6 | 12.6 | 12.6 | 12.6 | 12.6 |
| oil 21 | 8.4 | — | — | — | — |
| oil 17 | — | 8.4 | — | — | — |
| oli 18 | — | — | 8.4 | — | — |
| oil 19 | — | — | — | 8.4 | — |
| oil 20 | — | — | — | — | 8.4 |
| emulsifier 6 | 1.0 | 1.0 | 1.0 | 1.0 | 1.0 |
| AZCH 11 | 58.0 | 58.0 | 58.0 | 58.0 | 58.0 |
| Water 7 | 4.5 | 4.5 | 4.5 | 4.5 | 4.5 |
| wax 12 | 12.5 | 12.5 | 12.5 | 12.5 | 12.5 |
| Talc 9 | 2.0 | 2.0 | 2.0 | 2.0 | 2.0 |
| oil 14 | 1.0 | 1.0 | 1.0 | 1.0 | 1.0 |
| Hardness | | | | | |
| Penetration (mm) | 8.8 | 6.6 | 8.4 | 7.5 | 5.5 |
| Whiteness | | | | | |
| Wool (0 hr) | 29 | 21 | 23 | 17 | 19 |
| Wool (24 hr) | 68 | 26 | 26 | 21 | 16 |

EXAMPLE 5

In this Example further fomulations were made using the method of Example 1. The results are summarised in table 5 below.

TABLE 5

| Ingredient | Comparison 5.A | Example 5.1 |
|---|---|---|
| | % by weight | |
| wax 22 | 14.0 | 14.0 |
| wax 23 | 6.0 | 6.0 |
| AZCH 10 | 55.0 | 55.0 |
| Vol sil 1 | 19.0 | 14.0 |
| Oil 20 | 4.5 | 9.5 |
| Emulsifier 6 | 1.0 | 1.0 |
| Fragrance | 1.0 | 1.0 |
| Characteristics | | |
| Whiteness Wool | | |
| (0h) | 11 | 9 |
| after 24h | 32 | 19 |

From Table 5, it can be seen that the improvement in visible deposits increased from the time of initial application to a day later for the product according to the present invention compared with a similar product that is just outside the invention range.

Hardness Measurements by Penetrometer

Hardness measurements by a Lab Plant PNR 10 penetrometer were performed on a stick in the stick barrel using a Seta wax needle, mass =2.5 g, cone angle at the point of the needle specified to be 9°10'∓15' (ASTM D1321; IP376; DIN 51579), having a maximum drop of 50 mm. The stick was wound up to above the barrel surface, and then cut to leave a flat, uniform surface. The needle was carefully lowered to the stick surface, and then a penetration hardness measurement was conducted by allowing the needle in its holder to drop under its combined weight of 50 g for a period of 5 seconds after which the penetration depth is noted. This process was carried out at six different points on the stick surface.

The hardness reading quoted is the average value of the 6 measurements.

An appropriate hardness for antiperspirant material intended for use in an open-ended dispensing container is less than 30 mm, particularly in the range of 5 to 20 mm.

Measurement of Deposits

The procedure involves instrumentally applying a sample of an AP stick to a substrate using a pay-off rig under standardised conditions and then measuring the mean level of white deposits using image analysis.

I) Application of the Sample to the Substrate

The substrate was a 12×28 cm strip of Worsted wool fabric.

The AP sticks were previously unused and with domed top surface unaltered.

The pay-off rig comprised a flat base on which a flat substrate was attached by a clip at each end. A pillar having a mounting to receive a standard size stick barrel was mounted on an arm that was moveable horizontally across the substrate under the control of a pnuematic piston. The mounting for the stick barrel was spring biased to provide the same vertical force of the stick on the substrate each time.

Each stick was temperature conditioned in the laboratory overnight before the measurement was made. The stick was laterally passed across the substrate eight times. The substrate was carefully removed from the rig and the deposit score, i.e. assessment of white deposits, measured straight-away using image analysis.

II) Image analysis

The sample substrate was illuminated by high angle fluorescent tubes to remove shadowing. The image was recorded through a Sony XC77 camera with a Cosmicar 16 mm focal length lens. The camera was positioned vertically above a reference slide and the instrument calibrated. The sample substrate was placed under the camera and, an image captured. This was and then analysed using a Kontron IBAS image analyser to obtain the mean grey level. This notionally divided the image into a large array of pixels and measured the whiteness of each pixel. The whiteness was measured on a scale of 0 to 255, with 255 being whitest and 0 being black. It was assumed that low numbers indicate a clear deposit permitting the underlying substrate colour (grey or black) to be seen.

Sensory properties

Sensory properties are evaluated by a panel of evaluators. Evaluators undergo extensive training to ensure the consistency and sensitivity of their sensory assessments, involving assessing a range of standard systems that exemplify various levels for each key sensory attribute. The sensory properties reported herein include coolness on application or after 2 minutes, flakiness, drag, glide and filmy deposits.

Product Application

Products are applied by evaluators in a measured dose of 300mg +/−30 mg for sticks of coded formulations.

Protocol

Evaluators remove underarm hair 24 hours prior to testing. All testing is carried out in a controlled testing area, employing at least 14 evaluators. Evaluators are instructed to wash both their underarms and forearms with unperfumed Lux ™ soap in luke warm water and to dry thoroughly before applying test products.

Evaluators apply the first product to their left underarm and complete the relevant score sheet. The strength and intensity of each product's sensory attributes are recorded on a descriptively anchored and divided 10 cm line scale. When the left underarm score sheet is completed, a second product is applied to the right underarm and the process is repeated on a second score sheet. The evaluators' marks on the line scales are converted into scores on a 1–100 scale. Mean scores are then calculated for each sensory attribute for each product. Evaluators leave the products on their underarms unless any discomfort is reported.

We claim:

1. In an antiperspirant or deodorant cosmetic composition in the form of a stick which contains an antiperspirant or deodorant active comprising a continuous hydrophobic phase which contains a volatile silicone oil, a non-volatile hydrophobic oil and a wax structurant, a disperse aqueous phase and an emulsifier the improvement wherein the continuous phase comprises from 10 to 35% volatile silicone oil, and from 5 to 15% non-volatile hydrophobic oil, the disperse phase comprises from 40 to 75%, the antiperspirant or deodorant active comprises from 0.5 to 35%, the wax structurant comprises from 7 to 25%, the emulsifier comprises from 0.1 to 10%, and the composition contains up to 5% insoluble particulate materials, %s being by weight based on the composition.

2. A composition according to claim 1 in which the disperse phase comprises from 40 to 65%.

3. A composition according to claim 1 which contains from 8 to 20% by weight wax structurant.

4. A composition according to claim 1 in which the wax structurant has a melting point of from 55 to 85° C.

5. A composition according to claim 1, which contains not more than 2% of a C12 to C24 saturated linear aliphatic alcohol.

6. A composition according to claim 4 in which the wax structurant comprises castor wax and/or a paraffin wax.

7. A composition according to claim 1 which contains from 10 to 20% volatile silicone.

8. A composition according to claim 1 in which the non-volatile oil is selected from aliphatic esters, aromatic esters and hydrocarbons which are liquid at 25° C.

9. A composition according to claim 1, which contains the volatile silicone oil and non-volatile oil in a weight ratio of from 1:1 to 3:1.

10. A composition according to claim 1 which contains from 10 to 30% of a water-soluble antiperspirant active.

11. A composition according to claim 10 in which the weight ratio of antiperspirant active to non-volatile oil is from 1:1 to 4:1.

12. A composition according to claim 1 which contains from 1 to 5% by weight of a particulate insoluble material.

13. A composition according to claim 12 in which the particulate insoluble material is selected from talc, finely divided silica, clay, and particulate polyethylene.

14. A composition according to claim 1 which contains from 0.5 to 2% emulsifier.

15. A composition according to claim 1 in which said disperse phase contains up to 15% by weight of a polyhydric alcohol based on the formulation.

16. A composition according to claim 15 in which the polyhydric alcohol is selected from glycerol, and propylene glycol.

17. A process for the production of a cosmetic antiperspirant or deodorant emulsion stick comprising the steps of forming a hydrophobic mixture by mixing a volatile silicone oil, a non-volatile oil and a wax structurant at an elevated temperature or bringing the mixture to the elevated temperature at which the structurant melts or is dissolved or dispersed in the oils, thereby forming a mobile hydrophobic mixture, simultaneously or sequentially forming an aqueous phase contains water soluble or miscible constituents, shear mixing the mobile hydrophobic mixture with the aqueous phase in the presence of an emulsifier, and any insoluble particulate materials thereby forming an emulsion comprising a hydrophic continuous phase and a disperse aqueous phase, cooling or permitting the emulsion to cool to a temperature at which a solid is formed by the structurant structuring the continuous phase, in which the continuous phase comprises from 10 to 35% volatile silicone oil, and from 5 to 15% non-volatile hydrophobic oil, the disperse phase comprises from 40 to 75%, the antiperspirant or deodorant active comprises from 0.5 to 35%, the wax structurant comprises from 7 to 25%, the emulsifier comprises from 0.1 to 10%, the composition contains up to 5% insoluble particulate materials, %s being by weight based on the composition.

18. A cosmetic method for preventing or reducing perspiration or odors on human skin and particularly in armpits comprising applying topically to the skin an emulsion in the form of a stick contains an antiperspirant or deodorant active comprising a continuous hydrophobic phase which contains a volatile silicone oil, a non-volatile hydrophobic oil and a wax structurant, a disperse aqueous phase and an emulsifier in which the continuous phase comprises from 10 to 35% volatile silicone oil, and from 5 to 15% non-volatile hydrophobic oil, the disperse phase comprises from 40 to 75%, the antiperspirant or deodorant active comprises from 0.5 to 35%, the wax structurant comprises from 7 to 25%, the emulsifier comprises from 0.1 to 10%, the composition contains up to 5% insoluble particulate materials, %s being by weight based on the composition.

19. A composition according to claim 1 in which the disperse phase comprises from 45 to 60%.

20. A composition according to claim 1 which contains from 10 to 15% by weight wax structurant.

21. A composition according to claim 1, which contains the volatile silicone oil and non-volatile oil in a weight ratio of from 5:4 to 2:1.

22. A composition according to claim 1 which contains from 20 to 25% of a water-soluble antiperspirant active.

23. A composition according to claim 10 in which the weight ratio of antiperspirant active to non-volatile oil is from 2:1 to 10:3.

24. A composition according to claim 1 in which said disperse phase contains from 3 to 12% by weight of a polyhydric alcohol based on the formulation.

* * * * *